US011634358B2

(12) United States Patent
Duraisamy et al.

(10) Patent No.: US 11,634,358 B2
(45) Date of Patent: Apr. 25, 2023

(54) POLYCARBONATE DIOL COATING COMPOSITION FOR CAUSTIC AND UV RESISTANCE

(71) Applicant: Ferro Corporation, Mayfield Heights, OH (US)

(72) Inventors: Thirumalai Duraisamy, McDonald, PA (US); Kameron Gale, Washington, PA (US); Cindy Pankiewicz, Bridgeville, PA (US); George E. Sakoske, Independence, OH (US)

(73) Assignee: Ferro Corporation, Mayfield Heights, OH (US)

( * ) Notice: Subject to any disclaimer, the term of this patent is extended or adjusted under 35 U.S.C. 154(b) by 1232 days.

(21) Appl. No.: 15/860,833

(22) Filed: Jan. 3, 2018

(65) Prior Publication Data
US 2019/0202733 A1 Jul. 4, 2019

(51) Int. Cl.
| | | |
|---|---|---|
| *C03C 17/32* | (2006.01) | |
| *C03C 25/25* | (2018.01) | |
| *C03C 25/323* | (2018.01) | |
| *C03C 25/325* | (2018.01) | |
| *C03C 25/47* | (2018.01) | |
| *C08L 75/04* | (2006.01) | |
| *C08G 18/44* | (2006.01) | |
| *C08G 59/24* | (2006.01) | |
| *C08G 63/16* | (2006.01) | |
| *C08K 5/00* | (2006.01) | |
| *C08K 5/16* | (2006.01) | |
| *C07C 31/22* | (2006.01) | |
| *C01B 33/20* | (2006.01) | |
| *C03C 25/106* | (2018.01) | |
| *C08G 18/42* | (2006.01) | |
| *C09D 175/06* | (2006.01) | |
| *C08G 18/80* | (2006.01) | |
| *C08G 18/28* | (2006.01) | |

(52) U.S. Cl.
CPC ............ *C03C 17/322* (2013.01); *C01B 33/20* (2013.01); *C03C 25/106* (2013.01); *C03C 25/25* (2018.01); *C03C 25/323* (2013.01); *C03C 25/325* (2013.01); *C03C 25/47* (2018.01); *C07C 31/22* (2013.01); *C08G 18/2825* (2013.01); *C08G 18/4202* (2013.01); *C08G 18/4236* (2013.01); *C08G 18/44* (2013.01); *C08G 18/8074* (2013.01); *C08G 59/24* (2013.01); *C08G 63/16* (2013.01); *C08K 5/0025* (2013.01); *C08K 5/16* (2013.01); *C08L 75/04* (2013.01); *C09D 175/06* (2013.01); *C03C 2217/72* (2013.01); *C03C 2218/119* (2013.01); *C03C 2218/13* (2013.01); *C08K 2201/019* (2013.01)

(58) Field of Classification Search
CPC ............................... C01B 33/20; C07C 31/22
See application file for complete search history.

(56) References Cited

U.S. PATENT DOCUMENTS

| | | |
|---|---|---|
| 3,994,764 A | 11/1976 | Wolinski |
| 4,012,542 A | 3/1977 | Oswitch et al. |
| 4,649,062 A | 3/1987 | Kosiorek et al. |
| 4,677,179 A | 6/1987 | Hannemann |
| 5,178,685 A | 1/1993 | Borenstein et al. |
| 5,476,894 A | 12/1995 | Huber |
| 5,549,929 A | 8/1996 | Scheibelhoffer et al. |
| 5,643,657 A | 7/1997 | Dueber et al. |
| 5,647,901 A | 7/1997 | Brown |
| 5,855,820 A | 1/1999 | Chan et al. |
| 6,037,014 A | 3/2000 | Edgington |
| 6,077,563 A | 6/2000 | Kapp et al. |
| 6,140,386 A | 10/2000 | Vanderhoff et al. |
| 6,183,871 B1 | 2/2001 | Lee et al. |
| 6,617,371 B2 | 9/2003 | Ha |
| 7,365,105 B2 | 4/2008 | Kiefer-Liptak |
| 7,427,317 B2 | 9/2008 | Sloan |
| 7,547,369 B2 | 6/2009 | Khadilkar et al. |
| 8,088,206 B2 | 1/2012 | Bentley |
| 8,318,890 B2 | 11/2012 | Masubuchi et al. |
| 8,362,102 B2 | 1/2013 | Jeremic et al. |
| 8,377,516 B2 | 2/2013 | Pratt et al. |
| 8,816,012 B2 | 8/2014 | Brown et al. |
| 9,085,483 B2 | 7/2015 | Takeuchi et al. |
| 9,150,750 B2 | 10/2015 | Brown et al. |
| 9,522,983 B2 | 12/2016 | Eveson et al. |
| 9,782,794 B2 | 10/2017 | Miyazaki et al. |

(Continued)

FOREIGN PATENT DOCUMENTS

| | | | |
|---|---|---|---|
| CN | 101434773 A | * | 5/2009 |
| CN | 101434773 A | | 5/2009 |
| JP | 58-174477 A | | 10/1983 |

OTHER PUBLICATIONS

English translation of JP 58-174477 published Oct. 13, 1983, 17 pages.

(Continued)

*Primary Examiner* — Kelly M Gambetta
(74) *Attorney, Agent, or Firm* — Christopher Korff

(57) ABSTRACT

A curable glass coating composition including 5-70 wt % aliphatic polycarbonate diol, 5-60 wt % crosslinker, 1-20 wt % extender, 4-20 wt % fatty alcohol, and 2-30 wt % crystalline or amorphous powder filler material, and optionally 2-20 wt % aliphatic polyester polyol and 2-20 wt % cycloaliphatic epoxy. The coating composition can be applied to a glass substrate and cured to form a decorative cured polyurethane coating layer on the substrate that has improved caustic and UV resistance.

19 Claims, No Drawings

(56) References Cited

U.S. PATENT DOCUMENTS

| | | | |
|---|---|---|---|
| 2006/0160918 A1 | 7/2006 | Fujita et al. | |
| 2006/0260734 A1 | 11/2006 | Brown et al. | |
| 2007/0281136 A1 | 12/2007 | Hampden-Smith et al. | |
| 2008/0226863 A1 | 9/2008 | Prunchak et al. | |
| 2009/0035535 A1 | 2/2009 | Wachi et al. | |
| 2010/0004376 A1 | 1/2010 | Killilea et al. | |
| 2010/0071837 A1 | 3/2010 | Kapp et al. | |
| 2010/0113685 A1 | 5/2010 | Coward et al. | |
| 2010/0326593 A1* | 12/2010 | Harvey | B32B 7/12 156/275.7 |
| 2016/0333133 A1* | 11/2016 | Rukavina | B32B 27/08 |

OTHER PUBLICATIONS http://en.wikipedia.org/wiki/Dimethylformamide, five pages.
http://www.chemicalbook.com/ChemicalProductProperty_EN_CB4852296.htm, May 20, 2010, one page.
"Using VOC-Exempt Solvents to Formulate Compliant Coatings," http://infohouse.p2ric.org/ref/17/16643.pdf, Apr. 1996, seven pages.
Espacenet bibliographic data for CN101434773 published May 20, 2009, one page.
International Search Report for corresponding PCT/US2018/067836 dated Apr. 18, 2019, two pages.

* cited by examiner

POLYCARBONATE DIOL COATING COMPOSITION FOR CAUSTIC AND UV RESISTANCE

FIELD

The present subject matter relates to polyurethane coating compositions that are based on a reaction between polycarbonate diol and isocyanate, and which can be used to decorate glass substrates to produce a coating having improved caustic and ultraviolet (UV) resistance. The present subject matter also relates to methods of applying these polyurethane coating compositions to glass substrates, and glass substrates including these cured/crosslinked polyurethane coating compositions.

BACKGROUND

Organic coating/ink compositions that provide decorative and functional coatings for glass are known. In general, the organic coating/ink compositions are composed of a polymer resin, a crosslinking agent, performance additives and, optionally, a colorant. The conventional ink compositions, at ambient temperature (e.g. 25° C.) and pressure (e.g. 101.325 kPa), are usually in the form of a viscous liquid, or a solid that can be heated to melt into a liquid for applying to a substrate. The liquid compositions are applied to a glass substrate by silk screen or other application techniques, and the coating is heated to cure/crosslink the polymer resin in the coating composition to form a polymer film that is adhered to the surface of the glass substrate. However, the current polymeric resins used in these ink compositions are generally poorly resistant to weathering, chemicals including hot (about 75° C.) caustic baths, and abrasion, and have low impact strength.

When applied as a decorative coating to returnable beverage glass bottles, these coatings are repeatedly subject to UV exposure over the lifetime of the bottle, and when returned to the bottler for refilling, the bottles and coatings are washed in a heated caustic bath. The resistance of these conventional coating compositions to degradation caused by UV exposure and hot caustic bottle cleaning solutions are lower than desired.

Use of bis-phenol epoxies or aliphatic polyesters have been employed for the polymer resins in such coating compositions. However, crosslinked bis-phenol epoxies have poor UV resistance because of aromatic moieties present. Inclusion of UV additives in the epoxy ink formulations has not helped to achieve desired performance. Aliphatic polyesters are known for their UV stability but display poor hydrolytic stability when subject to a hot caustic wash. Therefore, there is a need for organic inks which have high resistance to hot caustic solutions and UV light exposure from being subject to outdoor weathering, particularly, when they are used for multiple trip applications in high UV exposure regions of the world.

As such, there is a need to provide improved compositions for coating glass that address the shortcomings of the previous glass coating compositions.

SUMMARY

The difficulties and drawbacks associated with previously known compositions are addressed in the present compositions, methods, and systems.

In one aspect, the present subject matter provides a curable glass coating composition including 5-70 wt % aliphatic polycarbonate diol, 5-60 wt % crosslinker, 1-20 wt % trimethylolpropane, 4-20 wt % fatty alcohol, and 2-30 wt % powder filler material, e.g. a zinc silicate frit powder. Such a coating composition can be applied to returnable glass bottles and shows a high resistance to degradation from exposure to UV radiation and hot (approximately 75° C.) caustic baths.

In another aspect, the present subject matter provides method of coating a glass substrate, comprising providing a curable glass coating composition including 5-70 wt % aliphatic polycarbonate diol, 5-60 wt % crosslinker, 1-20 wt % trimethylolpropane, 4-20 wt % fatty alcohol, and 2-30 wt % powder filler material, e.g. a zinc silicate frit powder. The coating composition is applied to the glass substrate, and is cured to form a coating on the glass substrate. The glass substrate may be a returnable glass bottle and the coating composition may include colorant such that the colored cured coating decorates the glass bottle.

As will be realized, the subject matter described herein is capable of other and different embodiments and its several details are capable of modifications in various respects, all without departing from the claimed subject matter. Accordingly, the drawings and description are to be regarded as illustrative and not restrictive.

DETAILED DESCRIPTION OF THE EMBODIMENTS

The present invention relates to organic curable glass coating compositions which have excellent resistance to degradation when exposed to UV radiation ("UV resistance") and to a hot caustic bath ("hydrolytic stability" or "caustic resistance"). By hot caustic bath, it is meant a caustic bath that is heated to about 70-80° C., or about 75° C. The improved UV resistance and hydrolytic stability are important for coating compositions that are applied to glass substrates, especially those substrates used as returnable beverage containers, which over the course of the their lifetimes are subjected to a cumulatively long duration of repeated exposure to UV radiation, and to multiple instances of being washed in hot caustic baths.

The present subject matter provides polycarbonate diol based curable glass coating compositions that are in solid or liquid form at ambient temperature (e.g. approximately 25° C.) and pressure (e.g. approximately 101.325 kPa). Such coating compositions may be used to decorate glass substrates, such as returnable (i.e. multiple use) and non-returnable (i.e. one-time use) beverage containers or bottles, perfume bottles, food containers, flat glass panels such as windows or structural glass, decorative glass, automotive glass, etc. For these applications, the coating compositions may include one or more colorants, the layers of which can be overlaid upon each other for multiple options for color decoration of the glass substrate. Once coated onto the glass substrate, the coating compositions are cured/crosslinked to form a polyurethane coating on the glass substrate that has improved UV and hot caustic resistance. The polyurethane coating can be used to provide indicia, coloring, or other decoration to the glass substrate.

Polycarbonate diol based curable glass coating compositions include an unreacted mixture of aliphatic polycarbonate diol and a crosslinker. Polycarbonate diol based polyurethanes provide good adherence to glass, UV stability, hardness, and chemical and hydrolytic stabilities. Polycarbonate diols can be included at 5-80 wt %, 5-70 wt %, 6-60 wt %, 7-50 wt %, or 8-40 wt % of the coating composition.

Useful polycarbonate diols are aliphatic polycarbonate diols of the following chemical formula I.

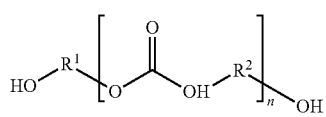

In the above chemical formula I, n can range from 2 to 20, $R^1$ and $R^2$ can comprise non-aromatic, open chain (linear or branched) or cyclic substituted or unsubstituted hydrocarbon compounds, and can be the same or different. In one embodiment, aliphatic (rather than aromatic) polycarbonate diols are used because aromatic moieties absorb UV radiation, resulting in the coating becoming brittle and causing delamination of the coating from glass substrates.

Suitable polycarbonate diols include homopolymers and copolymers of germinal diols, vicinal diols, 1,3-diols, 1,4-diols, and longer diols including hexanediol, pentanediol, and polycaprolactonediol, for example. The polycarbonate diols may have varying hydroxyl numbers, and may be in the form of waxy solids or in the form of liquids at ambient temperature and pressure. If liquid, the polycarbonate diol can have a Tg of less than ambient temperature. If solid, the polycarbonate diol can have a viscosity at 40° C. and 30 s-1 of 10-30 Pa·s. The polycarbonate diol can be a non-crystalline polymer with any one or more of an average molecular weight of 800-1200 g/mole, a hydroxyl number of 90-130 mg KOH/g, a water content of less than 1%, and an ash content (as sodium) of 100-200 ppm.

In one embodiment, the polycarbonate diol can include Oxymer™ HD112, or Oxymer™ M112 both sold by Perstorp Co., of Sweden. Oxymer™ M112 is a hydrophobic viscous liquid at room temperature (approximately 25° C.) and a Tg of −23° C. It is a non-crystalline polymer with an average molecular weight of approximately 1000 g/mole, a hydroxyl number of 104-120 mg KOH/g, a water content of 0.1%, an ash content (as sodium) of 150 ppm, a viscosity at 40° C. and 30 s−1 of 20 Pa·s. Oxymer™ HD112 is a solid at room temperature, has an average molecular weight of 1000 g/mol, a water content of less than 0.05%, and a hydroxyl number of 104-120 KOH/g. Other aliphatic polycarbonate diols can be used either alone or in combination with these, including Desmophen® C 2200 from Covestro Co. of Pittsburgh, Pa., USA, and Eternacoll® line of polycarbonate diols from UBE Industries Ltd. of Tokyo, Japan.

When the polycarbonate diol is in the form of a solid at ambient temperature and pressure, the curable glass coating composition may also be solid at ambient temperature and pressure. The coating composition may therefore be heated to a liquid state in order to coat it to a glass substrate, e.g. by screen printing techniques. When the polycarbonate diol is in the form of a liquid at ambient temperature and pressure, the coating composition may likewise be liquid at ambient temperature and pressure, and therefore may or may not require heating in order to coat it to a glass substrate.

The crosslinker in the coating composition is used to crosslink the polycarbonate diol, and the crosslinker can be blocked or unblocked. Suitable crosslinkers include isocyanates, including unblocked and blocked isocyanates. Other crosslinking agents can be used, including amine and melamine based crosslinkers (e.g. Cymel 303 available from Allnex Holding S.a.r.l. of Luxembourg), optionally in combination with isocyanate crosslinkers. One suitable crosslinker is Powderlink 1174, available from Cytec Industries Inc., Woodland Park, N.J., and which is blocked isocyanate of tetramethoxy methyl glycoluril. In embodiments that include the use of unblocked isocyanate, the isocyanate, because it is unblocked, is free to immediately react with the aliphatic polycarbonate diol upon mixing to thereby form a polyurethane coating. In these embodiments, the polycarbonate diol and unblocked isocyanate may be stored in separate containers (i.e. "two pot system") so that they do not to react by curing before application of the coating composition to a glass substrate. Instead, the polycarbonate may be mixed with the isocyanate just prior to application to a glass substrate.

In embodiments that include blocked isocyanate, the isocyanate, because it is blocked, is inhibited from immediately reacting with the aliphatic polycarbonate diol upon mixing. In one aspect, after the coating composition is applied to a glass substrate, the blocked isocyanate is heated to an unblocking temperature, which unblocks the isocyanate and makes it reactive, thus allowing the isocyanate to react with the polycarbonate diol to form a polyurethane coating on the glass substrate. In one aspect, the unblocking temperature is 75° C. to greater than 170° C., and up to about 240° C. The unblocking temperature should be greater than a temperature that causes the coating composition to change from a solid state to a liquid state. In these embodiments, the polycarbonate diol and blocked isocyanate may be stored together in a single container (i.e. "single pot system"), wherein the polycarbonate diol and blocked isocyanate can be mixed together at a time prior to application to a glass substrate and stored until needed for coating the substrate. The shelf life of a single pot coating composition may be up to six months or longer. Crosslinkers can be included at 5-60 wt %, 10-50 wt %, 20-40 wt %, 25-35 wt %, 20-60 wt %, 30-60 wt %, 40-60 wt %, or 50-60 wt % of the coating composition.

The isocyanate is not particularly limited by the present subject matter. Examples of suitable isocyanates include, but are not limited to, aliphatic isocyanates, cycloaliphatic isocyanates, aliphatic-cycloaliphatic isocyanates, aromatic isocyanates, and aliphatic-aromatic isocyanates. The isocyanates may be diisocyanates, triisocyanates, tetraisocyanates or polyisocyanates of higher order. In the preparation of the blocked isocyanates, any suitable isocyanate can be reacted with a blocking agent, such as diethyl malonate; 3,5-dimethylpyrazole; methylethylketoxime; caprolactam; or others, in order to form a blocked isocyanate having blocked NCO-groups, and have any one or more of an unblocking temperature of 100-400° C., a total NCO content of 10-20 wt %, a free NCO content of <0.5-5 wt %, a Tg of 30-100° C., NCO equivalent of 200-350 g/Eq, a density of 1.1-1.5 g/cm³, a bulk density of approximately 600-700 kg/m³, and a melting range of 40-150° C. In one embodiment the blocked isocyanate includes Vestgon® B 1530 produced by Evonik Industries of Germany, which has ε-Caprolactam blocked NCO-groups, an unblocking temperature of more than 170° C., a total NCO content of 14.8-15.7 wt %, a free NCO content of <1 wt %, a Tg of 41-53° C., NCO equivalent of approximately 275 g/Eq, a density of 1.14 g/cm³, a bulk density of approximately 670 kg/m³, and a melting range of 62-82° C.

In several embodiments, the coating composition may optionally include one or more of aliphatic polyester polyols and cycloaliphatic epoxies, each from about 2-30 wt %, 2-20 wt % or 5-15 wt % of the coating composition. The aliphatic polyester polyols and cycloaliphatic epoxies may be added to the coating composition before curing/crosslinking. It has been found that such additions of aliphatic polyester polyols and cycloaliphatic epoxies with polycarbonate diol in the coating composition before curing, may enhance the performance (e.g. UV resistance, mechanical resistance, and/or adhesion to the glass substrate) of the resulting cured polyurethane coating compared to a coating made only from polycarbonate diol, and without degrading the hot caustic resistance and hydrolytic resistance provided by the polycarbonate diol.

The aliphatic polyester polyol is not particularly limited, and may comprise a crystalline material having one or more of a hydroxyl number of 20-40 mg KOH/g, water content of 0.01-0.10 wt %, acid number of 1.0-3.0 mg KOH/g, equivalent weight of 1600-2000 g/eq OH, functionality of 1.0-3.0 eq. OH/mole, a viscosity at 80° C. of 3000-4000 cP, and a melting point of 40-100° C. One suitable aliphatic polyester polyol is Stepanpol® PC-205P-30 manufactured by Stepan Co. of Northfield Ill., which is a crystalline material having a hydroxyl number of 27-34 mg KOH/g, water content of 0.05 wt %, acid number of 2.0 mg KOH/g, equivalent weight of 1810 g/eq OH, functionality of 2.0 eq. OH/mole, a viscosity at 80° C. of 3500 cP, and a melting point of 54° C. Other aliphatic polyester polyols can be included in the coating composition.

The cycloaliphatic epoxies are not particularly limited, and may include those having one or more of a melting point of 0-20° C., a density of 900-1300 kg/m$^3$, and a dynamic viscosity of 0.1-4.0 Pa·s at 25° C. The cycloaliphatic epoxies may include 3,4-Epoxycyclohexylmethyl 3,4-epoxycyclohexanecarboxylate; diglycidyl 1,2-cyclohexanedicarboxylate; 3,4-Epoxycyclohexylmethyl-3',4'-epoxycyclohexane carboxylate modified ε-caprolactone. One suitable cycloaliphatic epoxy is Eponex™ 1510 produced by Momentive Corporation of Waterford, N.Y., USA, which is cyclohexanol, 4,4'-(1-methylethylidene)bis-, polymer with 2-(chloromethyl)oxirane (CAS number 30583-72-3), having a melting point of 10° C., a density of 1140 kg/m$^3$, and a dynamic viscosity of 1.8-2.5 Pa·s at 25° C. Another suitable cycloaliphatic epoxy is Epotec® YDH 3000, available from Aditya Birla Chemicals Ltd. of Bangkok, Thailand, which is a diglycidyl ether of hydrogenated bisphenol-A, having an epoxy equivalent weight of 220-240 g/eq, a viscosity at 25° C. of 2000-3000 cP, a maximum hydrolyzable chlorine content of 0.1%, an epoxide value of 4.16-4.55, a density at 25° C. of 1.14 g/ml, a maximum water content of 0.1%, a maximum ECH content of 10 ppm, and a flash point of 115° C. Other cycloaliphatic epoxies can be included in the coating composition. When a cycloaliphatic epoxy is included, a curing agent for the cycloaliphatic epoxy may be included at 0.1-5 wt %, and can include dicyandiamide. Suitable curing agents for the cycloaliphatic epoxy includes Amicure CG-1400, available from Evonik Corporation of Essen Germany.

The coating composition can include various additives in the uncured mixture, including an extender, fatty alcohol, crystal or glass frit powder material, a reaction catalyst, colorant, rheology modifiers, fillers, light stabilizers, antioxidants, etc. The additives can be included to provide various properties to, or enhance one or more characteristics of the coating composition or of the cured coating on the glass substrate.

In one embodiment, the coating composition includes an extender from 1-20 wt %, 1-10 wt %, or 2-8 wt % of the coating composition. In one aspect, the extender includes or consists of a polyhydric alcohol, for example trimethylolpropane (TMP). TMP is included to enhance the hardness of the cured coating on the glass substrate and to enhance the mechanical resistance of the cured coating to abrasion. Other extenders can be used, including caprolactone polyol, e.g. CAPA 3031 available from Perstorp of Sweden which is a very low molecular weight (300 mean molecular weight) trifunctional caprolactone polyol, in which all of the hydroxyl groups are primary; and hydroquinone dioxyethyl ether, e.g. Addolink 30/10 available from RheinChemie of Germany.

In an embodiment, the coating composition includes a fatty alcohol from 2-20 wt %, 2-15 wt %, or 2-10 wt % of the coating composition. The fatty alcohol can be included to provide various properties to, or enhance one or more characteristics of the coating composition or of the cured coating on the glass substrate. In one aspect, the fatty alcohol includes or consists of stearyl alcohol, which is included as a thickener to increase the viscosity of the coating composition so that the coating composition can be more easily applied by a particular coating technique, for example, screen printing. Other fatty alcohols can be used, including $C_4$ to $C_{26}$ fatty alcohols, e.g. myristyl, cetyl, lauryl and oleyl alcohols. The fatty alcohol can be saturated or unsaturated, or branched or unbranched. The role of fatty alcohol is to disperse ("wet") the resin system, thus lowering the viscosity of the coating composition and helping to improve the printing properties.

In an embodiment, the coating composition includes a crystalline or amorphous filler powder material from 2-30 wt %, 3-20 wt %, or 4-15 wt % of the coating composition. In one aspect, the crystalline or amorphous filler powder material includes or consists of zinc silicate frit powder, which is included to improve the printability of the coating composition, for example, in a screen printing process. The zinc silicate frit powder material may be crystalline $Zn_2SiO_4$. The zinc silicate frit powder material can be selected from any known phase of the Zn/Si phase system; however, zinc orthosilicate ($Zn_2SiO_4$) is preferred. Preferably, the zinc silicate material comprises at least about 90% by weight of crystalline $Zn_2SiO_4$. More preferably, the zinc silicate material comprises at least about 95% and up to 100% by weight of crystalline $Zn_2SiO_4$. A crystalline zinc silicate material suitable for use in the present invention can be prepared according to any of a number of well-known methods. For instance, $Zn_2SiO_4$ (CAS Registry No. 13597-65-4) can be prepared by heating zinc oxide (ZnO) and $SiO_2$ in a molar ratio of 2:1 at 1300° C. for 72 hours. One suitable zinc silicate material is GSGC 2099 available from Ferro Corporation, Mayfield Heights, Ohio. Other methods of preparing these and related materials are readily apparent to the skilled practitioner. Other crystalline or amorphous powder filler material may be used, including powders of alumina, zirconia, other glass frit (e.g. glass frit E-8046 with average particle size of 3 microns, available from Ferro Corporation, Mayfield Heights, Ohio), clay, boric oxide, silica, talc, etc. The particle size for the powder filler material is preferably in the range of 1 to 4 microns, more preferably about 1.8 microns.

In an embodiment, the coating composition includes a reaction catalyst to initiate or speed up the reaction between the polycarbonate diol and the crosslinker. The catalyst may be included in the coating composition from 0.001-0.01 wt %, or from 0.005-1.0 wt % of the weight of resin (e.g. one or more of polycarbonate diol, aliphatic polyester polyol, and cycloaliphatic epoxies) in the coating composition. The catalyst may include an organometallic complex that is free of one or more of tin, 2-ethylehexyl carboxylate, and 2-ethylehexanoic acid, includes 10-20% metal, and has a specific gravity at 25° C. of 1-1.15 g/ml. Suitable catalysts include any of the K-KAT line of catalysts available from King Industries Specialty Chemicals, Norwalk, Conn., including XK-640, XK-635, XK-620, XK-651, and XK-672. The catalyst may include basic and acidic amines including tertiary amine catalysts, triethylenediamine (TEDA, 1,4-diazabicyclo[2.2.2]octane), dimethyl cyclohexylamine (DMCHA), and dimethylethanolamine (DMEA), or lewis acids catalysts such as dibutyltin dilaurate.

The coating composition may also include a colorant in order to add color or other visual effects to the resulting cured coating for decorating the glass substrate. The colorant is not particularly limited, and may be organic or inorganic, included from 0.1-40 wt %, 1-30 wt %, or 5-20 wt % of the coating composition, and may include pigments, dyes, visual effects pigments, CICP's, etc., and combinations thereof.

The coating composition may also include 0.5-10 wt %, 0.5-5 wt %, or 0.1-3 wt % of a light stabilizer/light absorber, for example Tinuvin 770 by BASF, which is a hindered amine light stabilizer of bis(2,2,6,6,-tetramethyl-4-piperidyl) sebaceate, in combination with Tinunvin 900, which is a hydroxyphenyl-benzotriazole class UV light absorber.

The coating composition may also optionally include a defoamer at 0.1-5 wt %, e.g. Foamex N from Evonik Corporation of Essen Germany, which is dimethyl polysiloxane containing fumed silica, or others in the Foamex line including Foamex 10, 12, 20, 22, 24, 26, 28, 30, 32, 34, 800, 805 N, 810, 815N, 822, 823, 825, 830, 832, 833, 835, 840, 842, 843, 845, 855, 883, 1488, 3062, 7447, 8030, 8050, K3, K7, and Twin 4000; additional filler at 1-40 wt %, e.g. Cabosil line of fumed silicas available from Cabot Corporation of Boston, Mass., which are synthetic, amorphous, untreated fumed silicon dioxide, or Minstron Monomix available from Imerys Kaolin & Performance Additives Divisions of Paris, France, which is a platy, high purity talc; rheology and flow modifiers at 0.1-10 wt %, or 0.1-5 wt %, e.g. Modaflow acrylic resin available from Allnex of Belgium; an antioxidant at 0.1-2 wt %, e.g. Irganox 245 available from BASF, which is a sterically hindered phenolic antioxidant containing ethylenebis(oxyethylene)bis-(3-(5-tert-butyl-4-hydroxy-m-tolyl)-propionate); an adhesion promoter at 0.1-5 wt %, e.g. Silquest A-187 Silane available from Momentive Corporation of Waterford, N.Y., USA, which is gamma-glycidoxypropyltrimethoxysilane; 0-30 wt % or 12-18 wt % waxes, e.g. dodecanediol; and up to 5 wt %, e.g. 0.1-5 wt % glass, ceramic, or polymer spherical particles with an average size of from 100 nm to 20 µm. Other additives can be optionally included in the coating composition, including surfactants/dispersants at 0.1-10 wt %, such as DispersBYK-163, DispersBYK-321, which is a solution of a polyether modified polymethylalkylsiloxane including 48-49% concentration of 2-butoxyethanol, DispersBYK-405, and others in the DispersBYK line of dispersants available from BYK Additives and Instruments of Germany. The coating composition can optionally include adhesion promoters at 0.1-10 wt %, such as silane coupling agents available from Momentive Corp. of Waterford, N.Y., USA including Silquest A-1170, Silquest A-171, Silquest A-151NT, Silquest A-1524, Silquest A-174NT, Silquest A-186, Silquest A-1871, Silquest A-2120, and Silquest A-187, which is Gamma-Glycidoxypropyltrimethoxysilane.

The spherical particles optionally incorporated into the coating compositions at up to 5 wt % of the present invention may be organic or inorganic. Suitable inorganic microspheres are available commercially as inert filler materials, and include glass and ceramic microspheres. Either solid or hollow microspheres can be used. Inorganic microspheres are commercially available, and may comprise ceramics or glasses, including borosilicate glass and soda lime silica glass. Organic microspheres made from polyurethanes, acrylics, polyamides and other polymeric materials may also be used.

In several embodiments, the coating composition is free of bisphenol A and free of heavy metals including for example, lead, cadmium, chromium, nickel, vanadium, antimony and bismuth.

The present subject matter includes a method of coating or decorating a glass substrate. The substrate is not particularly limited, and may include for example, a returnable glass container such as a beverage bottle. The method can include applying one or more layers of the coating composition to the glass container, and curing the one or more layers. The layers may have different appearances (e.g. different colors) after curing, and may be applied in such an arrangement in order to provide indicia on the glass substrate, for example lettering, symbols, designs, or other indicia. The one or more layers may be overlapped with one another, either partially or completely, such that the colors of the one or more layers combine to provide a visible color that is a combination of the colors of the cured overlapping layers.

The method includes providing one or more coating compositions as described herein. A coating composition that is solid at ambient temperature and pressure ("solid coating composition"), and which could be applied by heating to melt the coating composition, may be prepared by heating to melt a polycarbonate diol that is solid at ambient temperature and pressure. Other optional ingredients, including the fatty alcohol, the extender (e.g. polyhydric alcohol), cycloaliphatic epoxies, aliphatic polyester, crystalline or amorphous zinc silicate material, and colorant, etc. are then mixed with the melted polycarbonate diol. This is followed by the addition of the crosslinker, which may be blocked or unblocked, to the composition. Lastly, the catalyst is mixed into the composition and the composition is optionally allowed to cool to solidify the composition.

A coating composition that is liquid at ambient temperature and pressure ("liquid coating composition") may be prepare by adding components in the same order as described for the solid coating composition, but this aspect does not necessarily require heating and subsequent cooling of the polycarbonate diol since the polycarbonate diol may be liquid at room temperature and pressure and the various components may be readily mixed with the liquid polycarbonate diol. In the event that the crosslinker is blocked, the coating composition can be stored for an amount of time before it is applied to a substrate.

The method includes applying one or more layers of the one or more coating composition to a glass substrate. The application method is not particularly limited, and can include for example, one or more of screen printing, digital printing, spraying, dip coating, curtain coating, roll coating, painting, pad printing, etc. When a solid coating composition is used, or even when a liquid coating composition is used, the application method may include heating the solid or liquid coating composition and optionally heating the fixtures used to apply the coating composition. This may include heating a screen of a screen printing apparatus or heating a nozzle of a spraying apparatus. Heating a solid coating composition may result in the solid coating composition changing from a solid to a liquid. Heating a liquid coating composition may result in a decrease of the viscosity of the coating composition.

When two or more layers of coating composition are applied to a glass substrate, the two or more layers may each include a liquid or solid coating composition. For example, a solid coating composition can be applied over another solid coating composition that has been solidified on the substrate, or over a liquid coating composition that has been dried on the substrate. A liquid coating composition can be applied over another liquid coating composition that has been dried on the substrate, or over a solid coating composition that has been solidified on the substrate. Additional layers, such as three or four or more total layers may be applied and cured on a substrate.

Once the layer(s) of coating composition is applied to the glass substrate, the layer(s) is cured. Curing of a layer of solid or liquid coating composition may include heating the coating composition so as to form one or more cured layers of a polyurethane coating on the substrate. Curing may comprise one or more heating cycles. In one embodiment, the coating composition layer(s) is heated to 350-450° F., or about 400° F., for 10-50 minutes, or about 30 minutes to cure the layer(s) of coating composition. If more than one layer of coating composition is applied to the glass substrate, curing of the layers may be performed individually, wherein one layer is cured before the next subsequent layer is applied, or collectively, wherein all the layers are cured at the same time, e.g. in a single heating step. If a liquid coating composition is used, the method may include drying of the layer of liquid coating composition to solidify the coating composition, which may precede a heating step to cure the coating composition.

In one embodiment, a solid coating composition is heated to liquid form and applied in liquid form as a first layer to a glass substrate. The layer of the coating composition is then cooled to form a solidified first layer on the substrate, but is not yet cured. Then a second layer of the same or different coating composition is applied to the glass substrate, optionally at least partially covering the solidified first layer. The second layer may be formed from either a solid or liquid coating composition. After the second layer is applied, the first and second layers are heated to form cured polyurethane first and second layers on the glass substrate. Other additionally layers of coating composition may be applied and cured to the glass substrate, e.g. at least partially covering the first or second layers, either before or after curing the first and second layers.

The cured first and second layers of cured inventive coating compositions, and any additional cured layers, may form indicia, e.g. printing, symbols, marks designs, or logos, on the glass substrate.

Unless otherwise noted, all compositional percentages disclosed herein are by wt % unless otherwise noted, and are given for a composition prior to reaction and curing. Numerical ranges of various components that are bounded by zero on the lower end (for example, 0-7% by weight) are intended to provide support for the concept "up to [the upper limit]" of the component. For example, "0-7% by weight" is intended to provide support for "up to 7% by weight" as well as a positive recitation that the component is present at some amount, for example at 0.01 wt % or 0.1 wt %, and in an amount that does not exceed the upper limit. An example of the latter is a recitation that the component is present, "provided the amount does not exceed 7 wt %."

All ranges disclosed herein are to be understood to encompass the beginning and ending range values and any and all subranges therein. For example, a stated range of "7 wt % to 17 wt %" should be considered to include any and all subranges between (and inclusive of) the minimum value of 7 wt % and the maximum value of 17 wt %. That is, all subranges are included, beginning with a minimum value of 7 wt % or more, and ending with a maximum value of 17 wt % or less, e.g., 7.0 wt % to 8.7 wt %, 9.3 wt % to 12.9 wt %, 11.7 wt % to 17 wt %, etc.

EXAMPLES

In order to further assess the various aspects and benefits of the present subject matter, a series of investigations were undertaken to evaluate the coating compositions and cured polyurethane layers formed on glass substrate.

Several example curable glass coating compositions were prepared, coated to a glass substrate, and cured to produce a cured polyurethane coating on the glass substrate. Table 1 shows the weight percentage (wt %) of components for Example 1, which is a solid coating composition in accordance with the present subject matter that can be cured on a glass substrate to produce a white cured polyurethane coating on the glass substrate.

TABLE 1

| Example 1 | |
|---|---|
| Component | Weight % |
| waxy solid polycarbonate diol | 8-40 |
| aliphatic polyester polyol | 2-30 |
| capped crosslinker | 20-40 |
| catalyst | 0.005-1.0 |
| extender | 1-10 |
| flow modifier | 0.1-5 |
| fatty alcohol | 4-10 |
| Dispersant 1 | 0.1-5 |
| Dispersant 2 | 0.1-5 |
| adhesion promoter | 0.1-5 |
| zinc silicate powder filler material | 4-15 |
| filler 1 | 1-20 |
| filler 2 | 1-20 |
| TiO$_2$ 2220 pigment | 10-20 |
| Nubix V-8 pigment | 0.1-1 |
| AR Blue pigment | 0.1-1 |
| light stabilizer 1 | 0.5-5 |
| light stabilizer 2 | 0.5-5 |
| antioxidant | 0.1-2 |

The solid coating composition of Example 1 was prepared by a pre-melt process, wherein a waxy solid polycarbonate diol, aliphatic polyester polyol, fatty alcohol, and an extender are pre-melted in a heated container at 200° F., followed by dispersion of capped crosslinker (e.g. capped isocyanate) with high shear mixing while the vat being heated. All other ingredients were added one by one and mixed. The catalyst was added at the last stage.

Table 2 shows the wt % of components for Example 2, which is a liquid coating composition in accordance with the present subject matter that can be cured on a glass substrate to produce a red cured polyurethane coating on the glass substrate.

TABLE 2

Example 2

| Component | Wt % |
| --- | --- |
| Polycarbonate Diol | 8-40 |
| PC/Capped Isocyanate solution | 40-60 |
| Catalyst | 0.005-1.0 |
| Extender in Dipropylene Glycol Solution | 1-10 |
| flow modifier | 0.1-5 |
| defoamer | 0.1-5 |
| Dispersant | 0.1-5 |
| adhesion promoter | 0.1-5 |
| zinc silicate powder filler material | 4-15 |
| filler | 1-20 |
| Cinilex DPP red pigment | 0.1-5 |
| HF3S Red pigment | 0.1-5 |
| light stabilizer 1 | 0.5-5 |
| light stabilizer 2 | 0.5-5 |
| antioxidant | 0.1-5 |

The liquid coating composition of Example 2 was prepared by a method similar to example 1. PC/capped isocyanate solution is a solution of 63 wt % capped isocyanate in polycarbonate diol. The extender in Dipropylene glycol solution is 70 wt % extender dissolved in dipropylene glycol.

The coating compositions of Examples 1 and 2 were applied to, and cured on, glass substrates, and compared to cured layers formed on glass substrates from curing the following Comparative Example 1 and Comparative Example 2, which are known coating compositions.

Comparative Example 1 is a commercially available BPA epoxy formulation, 90-100 HTP white, available from Ferro Corporation, Mayfield Heights, Ohio, and as shown in Table 3.

TABLE 3

Comparative Example 1

| Component | Wt % |
| --- | --- |
| Epoxy Resin EPON 1001F | 20-60 |
| Epoxy EPON 828 Bisphenol A | 1-15 |
| Dodecanediol 1,12 | 10-30 |
| Surfactant BYK 321 | 0.1-5 |
| Modaflow | 1-10 |
| AMICURE CG-1400 | 1-10 |
| BYK 405 | 0.1-5 |
| Organosilane A-187 | 1-10 |

TABLE 3-continued

Comparative Example 1

| Component | Wt % |
| --- | --- |
| Cabosil TS 720 | 1-10 |
| Titanium Oxide KRONOS 2160 | 10-30 |
| NUBIX V-8 | 0.05-1 |
| NUBIPERF AR | 0.05-1 |

Comparative Example 2 is a polyester based HTP overprintable ink formulation as shown in Table 4.

TABLE 4

Comparative Example 2

| Component | Wt % |
| --- | --- |
| Rucote 102 binder | 20-40 |
| Powderlink 1174 crosslinker | 20-40 |
| PE400 floW aid | 1-10 |
| BYK 163 dispersant | 0.1-5 |
| R-902 TiO2 pigment | 10-30 |
| Cabosil TS720 | 1-10 |
| Masil 750 Wetting aid | 0.1-5 |
| A-187 adhesion promoter | 0.1-5 |
| Nacure 5225 catalyst | 0.05-1 |

As shown below in Table 5, the properties of cured polyurethane coatings of Examples 1 and 2 on glass substrates are compared to the properties of the Comparative Examples 1 and 2 and to known properties of a cured polyurethane coating produced from cycloaliphatic epoxies.

TABLE 5

Results

| Polymeric Resins | UV | Caustic | Hydrolytic Resistance | UV-Caustic combined | Mechanical Resistance |
| --- | --- | --- | --- | --- | --- |
| Comparative Example 1 | Poor | Very good | Very good | Poor | Very Good |
| Cycloaliphatic Epoxies | Very good | Poor | Poor | Poor | Very Good |
| Comparative Example 2 | Very good | Poor | Very Poor | Poor | Good |
| Examples 1 and 2 | Excellent | Very good | Very Good | Very Good | Good |

As depicted in Table 5, Comparative Example 1, which includes BPA epoxies, produces a cured polyurethane coating having poor UV resistance and good caustic, hydrolytic and mechanical resistance (i.e. high hardness). Use of aliphatic polyester polyols in Comparative Example 2 produces a polyurethane coating that shows high UV stability, improved adhesion to glass, and good mechanical resistance, but poor caustic resistance and very poor hydrolytic resistance. Cycloaliphatic epoxies provide polyurethane coatings with very good mechanical resistance and UV stability, but poor adhesion to glass, and poor caustic and hydrolytic resistance. Inventive Examples 1 and 2 produce excellent UV resistance, very good caustic and hydrolytic resistance, and good mechanical resistance.

Another formulation of an inventive solid coating composition according to the present subject matter is shown below as Example 3 in Table 6.

TABLE 6

Example 3

| Ingredients | Wt % |
| --- | --- |
| polycarbonate diol | 8-40 |
| cycloaliphatic epoxy | 2-30 |
| Dispersant | 0.1-5 |
| Cinilex DPP Red pigment | 10-20 |
| HF3S Red pigment | 10-20 |
| reaction catalyst | 0.001-0.01 |
| filler | 1-20 |
| flow modifier | 0.1-5 |
| cycloaliphatic epoxy curing agent | 0.1-5 |
| adhesion promoter | 0.1-5 |
| light stabilizer 1 | 0.5-5 |
| light stabilizer 2 | 0.5-5 |
| antioxidant | 0.1-2 |
| capped isocyanate | 20-40 |
| Fatty alcohol | 4-20 |
| Kronos $TiO_2$ 2220 pigment | 5-20 |
| Huberbrite 1 pigment | 5-20 |

Another example of an inventive solid coating composition, according to the present subject matter is shown below as Example 4 in Table 7.

TABLE 7

Example 4

| Ingredients | Wt % |
| --- | --- |
| waxy solid polycarbonate diol | 8-40 |
| aliphatic polyester polyol | 2-30 |
| cycloaliphatic epoxy | 2-20 |
| capped isocyanate | 20-40 |
| cycloaliphatic epoxy curing agents | 1-4 |
| extender | 1-10 |
| flow modifier | 1-5 |
| fatty alcohol | 2-10 |
| Dispersant 1 | 0.1-5 |
| Dispersant 2 | 0.1-5 |
| adhesion promoter | 0.1-5 |
| light stabilizer 1 | 0.5-5 |
| light stabilizer 2 | 0.5-5 |
| antioxidant | 0.1-2 |
| E-8046 powder filler material | 2-20 |
| filler | 1-10 |
| TiO2 2220 pigment | 5-20 |
| V-8 pigment | 0.1-1 |
| AR Blue pigment | 0.1-1 |

The solid coating compositions of Examples 3 and 4 can be applied as an overprinting ink over another inventive solid or liquid coating composition that has been applied to a glass substrate. Examples 3 and 4 are solid at room temperature, and can have a melting temperature that is lower than a melting temperature of an underlying solid coating composition by about 20° F. or greater. In this way, Examples 3 and 4 can be melted and applied as a liquid to the underlying solid coating composition without melting the underlying solid coating composition. Inventive Examples 3 and 4 produce excellent UV resistance, very good caustic and hydrolytic resistance, and good mechanical resistance.

Many other benefits will no doubt become apparent from future applications and developments of this technology.

All patents, applications, standards, and articles noted herein are hereby incorporated by reference in their entirety.

The present subject matter includes all operable combinations of features and aspects described herein. Thus, for example if one feature is described in association with an embodiment and another feature is described in association with another embodiment, it will be understood that the present subject matter includes embodiments having a combination of these features.

As described hereinabove, the present subject matter solves many problems associated with previous strategies, systems and/or devices. However, it will be appreciated that various changes in the details, materials and arrangements of components, which have been herein described and illustrated in order to explain the nature of the present subject matter, may be made by those skilled in the art without departing from the principle and scopes of the claimed subject matter, as expressed in the appended claims.

What is claimed is:

1. A curable glass coating composition including:
    5-70 wt % aliphatic polycarbonate diol,
    5-60 wt % crosslinker,
    1-20 wt % trimethylolpropane,
    4-20 wt % fatty alcohol, and
    2-30 wt % powder filler material,
    wherein the powder filler material is zinc silicate powder, and
    wherein the composition is free of bisphenol A and free of heavy metals including lead, cadmium, chromium, nickel, vanadium, antimony and bismuth.

2. The composition according to claim 1, including:
    10-60 wt % aliphatic polycarbonate diol,
    10-50 wt % the crosslinker,
    5-15 wt % trimethylolpropane,
    10-15 wt % fatty alcohol, and
    10-20 wt % powder filler material.

3. The composition according to claim 1, further including 2-20 wt % aliphatic polyester polyol.

4. The composition according to claim 1, further including 2-20 wt % cycloaliphatic epoxy.

5. The composition according to claim 1, further including a 2-20 wt % colorant.

6. The composition according to claim 1, further including 0.1 up to 5 wt % glass, ceramic, or polymer spherical particles from 100 nm to 20 um in average size.

7. The composition according to claim 1, wherein at 101.325 kPa the polycarbonate diol is solid at or below 25° C. and has a melt temperature above 25° C.

8. The composition according to claim 1, wherein the crosslinker comprises a blocked isocyanate and the composition can be cured by heating the composition.

9. The composition according to claim 1, wherein the crosslinker comprises an unblocked isocyanate and the composition can be cured by drying the composition.

10. A method of coating a glass substrate, comprising:
    providing a curable glass coating composition including
        5-70 wt % aliphatic polycarbonate diol,
        5-60 wt % crosslinker,
        1-20 wt % trimethylolpropane,
        4-20 wt % fatty alcohol, and
        2-30 wt % powder filler material, wherein the powder filler material is zinc silicate powder, and wherein the composition is free of bisphenol A and free of heavy metals including lead, cadmium, chromium, nickel, vanadium, antimony and bismuth, applying the coating composition to the glass substrate, and curing the coating composition to form a coating on the glass substrate.

11. The method according to claim 10, wherein the coating composition comprises:
    10-60 wt % aliphatic polycarbonate diol,
    10-50 wt % crosslinker,
    5-15 wt % trimethylolpropane,
    10-15 wt % fatty alcohol, and
    10-20 wt % powder filler material.

12. The method according to claim 10, wherein:
    the coating composition further includes at least one of 2-20 wt % aliphatic polyester polyol, 2-20 wt % cycloaliphatic epoxy, and 2-20 wt % colorant.

13. The method according to claim 12, wherein the coating composition further includes 0.1-5 wt % glass, ceramic, or polymer spherical particles from 100 nm to 20 um in size.

14. The method according to claim 10, wherein:
    the coating composition is solid at 101.325 kPa and at or below 25° C., and has a melt temperature above 25° C.,
    the method further includes heating the coating composition to the melt temperature to melt the coating composition, and
    applying includes screen printing the melted coating composition to the glass substrate.

15. The method according to claim 10, wherein:
    the coating composition is liquid at 101.325 kPa and at 25° C. and has a melt temperature below 25° C., and
    applying includes screen printing the liquid coating composition to the glass substrate.

16. The method according to claim 10, wherein the glass substrate is a returnable glass beverage container.

17. The method according to claim 10, wherein the coating composition further includes 0.1-5 wt % glass, ceramic, or polymer spherical particles from 100 nm to 20 um in average size.

18. The method according to claim 10, wherein:
    the crosslinker comprises a blocked isocyanate, and
    curing includes heating the coating composition.

19. The method according to claim 10, wherein:
    the crosslinker comprises an unblocked isocyanate, and
    curing includes drying the coating composition.

\* \* \* \* \*